(12) United States Patent
Basagañas Millan

(10) Patent No.: US 6,850,697 B2
(45) Date of Patent: Feb. 1, 2005

(54) HEATER DEVICE FOR ACTIVE SUBSTANCES

(75) Inventor: Jordi Basagañas Millan, Barcelona (ES)

(73) Assignee: DBK Espana, S.A., Barcelona (ES)

(*) Notice: Subject to any disclaimer, the term of this patent is extended or adjusted under 35 U.S.C. 154(b) by 0 days.

(21) Appl. No.: 10/406,641

(22) Filed: Apr. 2, 2003

(65) Prior Publication Data

US 2003/0231876 A1 Dec. 18, 2003

Related U.S. Application Data

(63) Continuation of application No. PCT/ES00/00368, filed on Oct. 3, 2000.

(51) Int. Cl.[7] .............................. A61M 16/00; F24F 6/00
(52) U.S. Cl. ........................................ 392/390; 392/392
(58) Field of Search ................................. 392/386, 390, 392/392, 394, 395; 43/125, 129, 130; 439/11, 13; 122/366

(56) References Cited

U.S. PATENT DOCUMENTS 6,278,840 B1    8/2001    Basaganas Millan

FOREIGN PATENT DOCUMENTS

| EP | 0 334 785 | 9/1989 |
|---|---|---|
| EP | 0 945 062 | 9/1999 |
| ES | 1 005 422 | 11/1988 |
| ES | 2 068 825 | 11/1988 |
| ES | 1 009 203 | 7/1989 |
| ES | 2 137 111 | 12/1999 |

*Primary Examiner*—Sang Y. Paik
(74) *Attorney, Agent, or Firm*—Katten Muchin Zavis Rosenman

(57) ABSTRACT

A heater device includes an external casing (1), an inner part (2), a pair of contact elements (3) and (3'), and a jack plug (4). Contact elements (3) and (3') define pairs of salient projections (17) and (18) which allow connection of the jack plug (4) in two positions of rotation, at 90° to each other, and prevent connection in an intermediate position. The heater device operates to heat a wick which emerges from a vessel containing an active substance to cause the evaporation of the substance. The vessel is retained on the lower end of the heather device by a ring (26) provided on inner part (2).

7 Claims, 5 Drawing Sheets

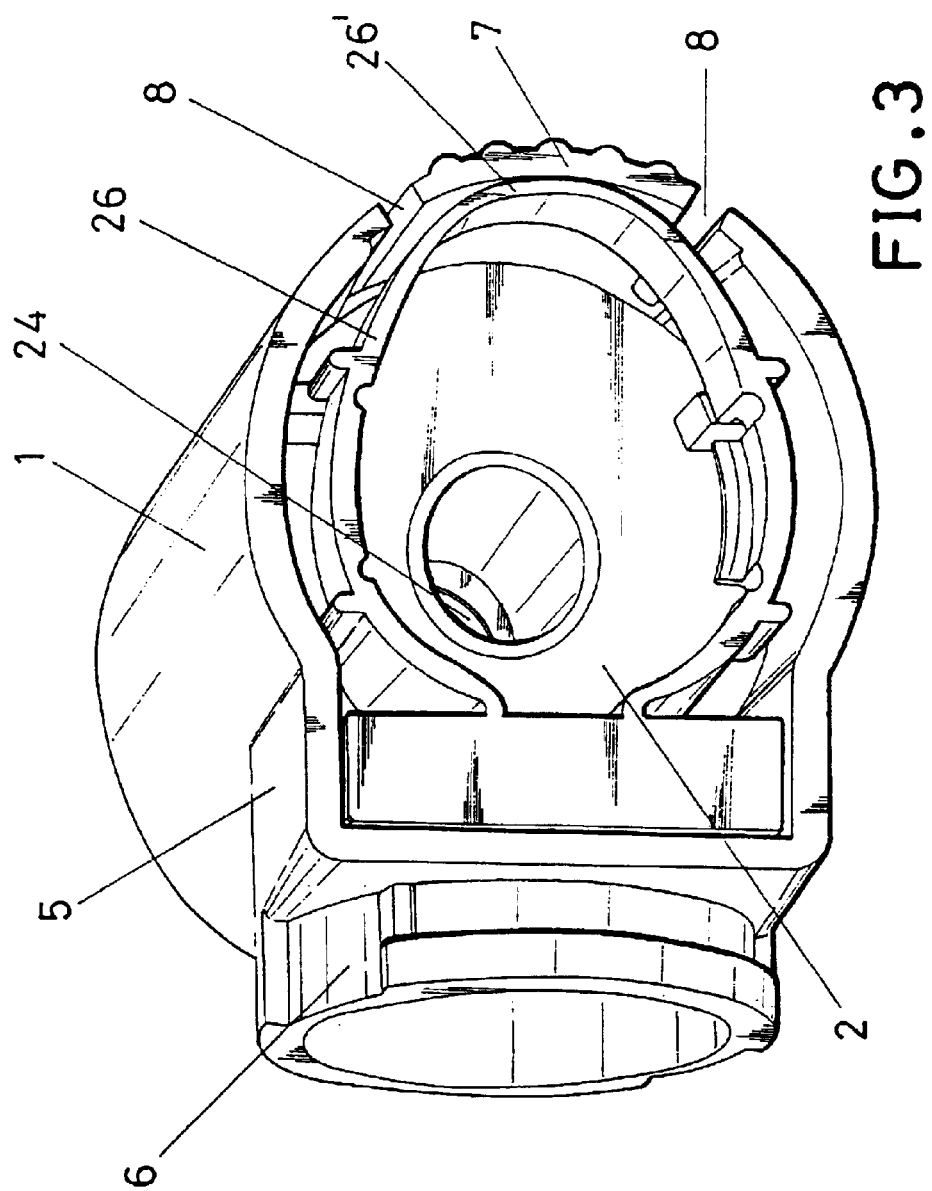

HEATER DEVICE FOR ACTIVE SUBSTANCES

This application is a continuation of International Application Number PCT/ES00/00368 filed Oct. 3, 2000.

OBJECT OF THE INVENTION

The present invention relates to a heater device for active substances meant to heat a wick soaked in a-volatile active substance (such as an insecticide, air freshener, etc.) which is contained in a vessel which can be coupled to the heater device itself, so that by capillary action the active substance rises through the wick which emerges from said vessel into a neck provided in the device, in which are provided heating elements which are actioned by the corresponding plug of the device, which can be plugged into an electric power network.

The object of the invention is to provide a heating device based on electrical resistors, consisting of four single parts and optionally a fifth part, duly coupled to each other without requiring additional means of any sort, neither for attachment nor release of the vessel from the heating device, nor for establishing the direct connection of said contacts to the heating elements, and in turn a direct connection to the jack plug, such that said switch is permanently joined to the device and activation/deactivation of said device is achieved by a rotation of the plug relative to the general body of the device.

BACKGROUND OF THE INVENTION

Devices are known which are plugged into the electricity mains connection of a household or any other premises in order to achieve evaporation of an active substance, whether for an air freshener or to produce vapors to eliminate insects, bacteria, fungi, etc. which devices are based on a jack plug which through contacts provide electrical power to a heater, which may be comprised of resistors, which heat a wick which rises from a vessel containing the active substance, so that heating of the wick and thereby of the substance which flows in it by capillary action will cause the release of the active substance.

Devices of this type, although practical, easy to use and clean, without causing any hindrance, suffer from certain drawbacks and disadvantages such as a complex assembly of their components and the need of a switch for disconnection from the power supply, or disconnection by unplugging directly.

Also worth mentioning is that the leads which establish connection between the corresponding contacts and the resistors require handling in their assembly, stripping of the plastic insulation which coats the leads, cutting excess wire of the resistances themselves which must be arranged around the wick to generate the heat for evaporation of the liquid or active substance which, by capillary action, rises in said wick, and a connection system between each wire and the corresponding electrical power lead.

Also troublesome is the method for attaching the vessel to the device which in most known devices requires a special handling, as although devices exist in which coupling/removal of the vessel is simple, this is in expense of a minimum reliability of the attachment of said vessel as it occasionally releases on its own and falls to the ground due to its weight.

DESCRIPTION OF THE INVENTION

The device disclosed has been conceived to solve the abovementioned problems, as well as to provide additional characteristics as compared to conventional devices.

More specifically, the device of the invention is based on one hand in that it can only comprise four parts, optionally five, thereby providing a great simplicity of assembly, manufacture, reliability and use, which parts consist of an outer casing, an inner part for mounting the corresponding contacts, which contacts are considered as the third part, with the plug-bearing set as well as the plug itself forming the fourth part, while the fifth, optional part is a lid for the inner mount which covers the housing of the heater elements in the second part, with the second part provided with an axial neck which allows the wick to pass and elastic means for retaining and simple release of the corresponding vessel containing the active substance which is to be evaporated.

Both the outer casing and the inner part of body are preferably made of a plastic material, such as a polyolefin of a polyamide type (PA) or polypropylene (PP) or polybutyl terephthalate (PBT) or polyoxymethylene (POM) or polyphenyl sulphur (PPS), such that the casing is hollow and presents a fully open base for assembly of the inner part or body, a lateral projection with a neck for assembly of the corresponding plug carrier, which consists of two pins embedded in a molded part which forms the plug itself, such that this molded part has a pair of projections on its inner face which together with ribs provided for such purpose in the lateral neck of the case, form a means of coupling and retention of said plug on the casing, such that the plug is prevented from separating from the casing yet allowed to rotate about it, with the particular characteristic that the plug pins emerge through their inner part as axial segments, the ends of which stop against the contacts provided for such purpose and duly placed in the inner part or body, which contacts have a special configuration so that each one has an upper part in the form of a bridge for assembly and correct attachment to a wall of the inner part or body, as well as two salient parts staggered respect to each other and elastically deformable, on which may incide the ends of the inner extensions of the plug pins. The contact elements are arranged so that connection to the plug is established at two positions, at 90° to each other, while in an intermediate position the ends of the plug are in an area in-between the contacts, which area is recessed with respect to the salient parts against which stop the ends of the plug tabs, defining an inoperative position where there is no contact at all, therefore providing in this intermediate position which is unaligned with the others a deactivation of the device, that is, a position in which the electrical power supply is cut off without requiring a switch of any kind, nor conducting wires as in conventional systems since the electrical resistors to be placed on the passage neck provided on the inner part or body will make contact and be attached to the pins corresponding to the elements which form the aforementioned contacts.

Also worth mentioning is that the inner part or body is provided, in correspondence with the walls for mounting the contacts, with grooves or depressions in which the excess wire of the heating resistors is folded and straightened, thus avoiding the need to cut said excess wire segments which are suitably positioned as described above.

A further novel characteristic is that the inner part is provided with tabs which are arranged preferably in a diametric opposition which form the means for attachment and securing of said part inside the casing when it is inserted to its maximum penetration position in the casing.

Another novel characteristic is that said inner part is provided on its lower part, that is, in the area where the vessel is placed which contains the active substance to be evaporated, with an elastically deformable ring which in its resting positions tends towards an oval shape in order to retain the vessel in this position, through the latter's neck, while release of said vessel is achieved by pushing inwards an elastic sector of the general casing which incides on the narrowest part of said ring making its sides open and thereby resulting in the release of the vessel retained by these sides.

The fifth optional part is meant to be a lid for the previous part at the place where the heating elements and their wires are housed in the inner body. Its novel characteristic is that it may be used or not, without substantially altering the evaporation performance of the device as a whole. It stands out in that it is positioned self-centered around the inner part or body for the wick, and in that it also covers the heater housing, which may be for example resistors. This optional lid is kept in position by friction of the edge of its circular orifice on three small ribs parallel to the chimney axis made at 120° and in relief on the outer walls of the neck of the chimney of the inner part or body.

DESCRIPTION OF THE DRAWINGS

As a complement of this description and in order to aid a better understanding of the characteristics of the invention, in accordance with a preferred embodiment, a set of drawings is accompanied as an integral part of the description where, for purposes of illustration only and in no way meant as a definition of the limits of the invention, the following is shown:

FIG. 3.—Shows a bottom perspective view of the device without the plug but revealing the shape of the elastic deformable bottom ring of the inner part meant for attachment and securing of the vessel which contains the active substance, as well as the elastic inner sector of the inner casing by which said inner ring is pressed on to release said vessel.

PREFERRED EMBODIMENT OF THE INVENTION

Figure 1:
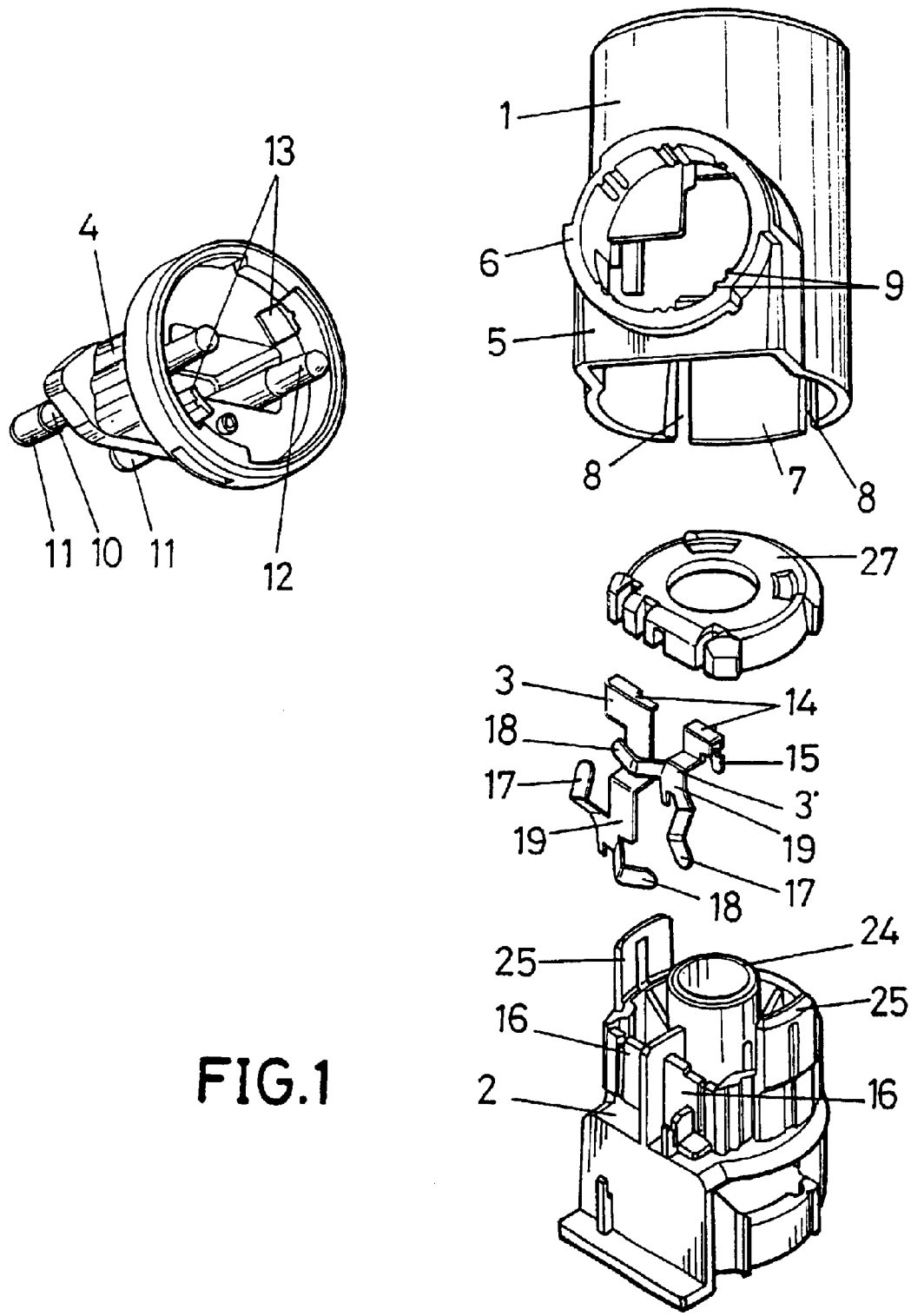
FIG. 1.—Shows a general perspective view of the four components or fundamental parts plus an optional part which make up the heating device for active substances in accordance with the object of the present invention, and whose five components are the outer casing, the inner part for mounting the two contacts, also shown in the figure, the corresponding jack plug and the optional lid.

As shown in the abovementioned drawings, the device of the invention comprises four fundamental parts or elements and a fifth optional part, the first of which corresponds to a general casing (1) with a cylindrical shape, the second to a part (2) which is to be mounted inside the former, the third consists of two elements (3) and (3') which form the device contacts, the fourth component or part consists of the corresponding jack plug (4) and the fifth optional part (27) which is circular and flat in shape with edges, is used as a lid for the housing provided for one or more heating elements (20) and the corresponding attachment elements (21).

As regards the casing (1), it is open on the bottom and in correspondence with its lateral surface it is provided with a projection (5) from which branches a cylindrical body (6) in which is coupled the jack plug (4), which casing (1) in correspondence with the end described as its bottom open end comprises an elastic sector (7) which is formed between two axial slits (8) of the general cylindrical body of the casing (1), such that said elastic sector (7) is meant to carry out the function which corresponds to releasing the vessel which contains the active substance which is to be evaporated, as described further below.

Inside cylindrical neck (6) are provided a number of projections (9) with a length shorter than the height of the cylindrical neck (6).

Jack plug (4) consists of a body obtained by molding and in which are embedded the corresponding pins (10), with outer segments (11) for contact with the corresponding electrical power supply plug and with emerging internal segments (12) for contact to contacts (3) and (3'). Additionally, the body of the jack plug (4) has inferior projections (13) which provide a means for retention when coupling the body of plug (4) inside neck (6) of casing (1), when said projections (13) pass the inner end of ribs (9) of neck (6), thereby retaining plug (4) in casing (1) without allowing axial removal but allowing rotation, so that plug (4) may be positioned as the user wishes but always allowing its rotation and not its axial displacement.

Figure 2:
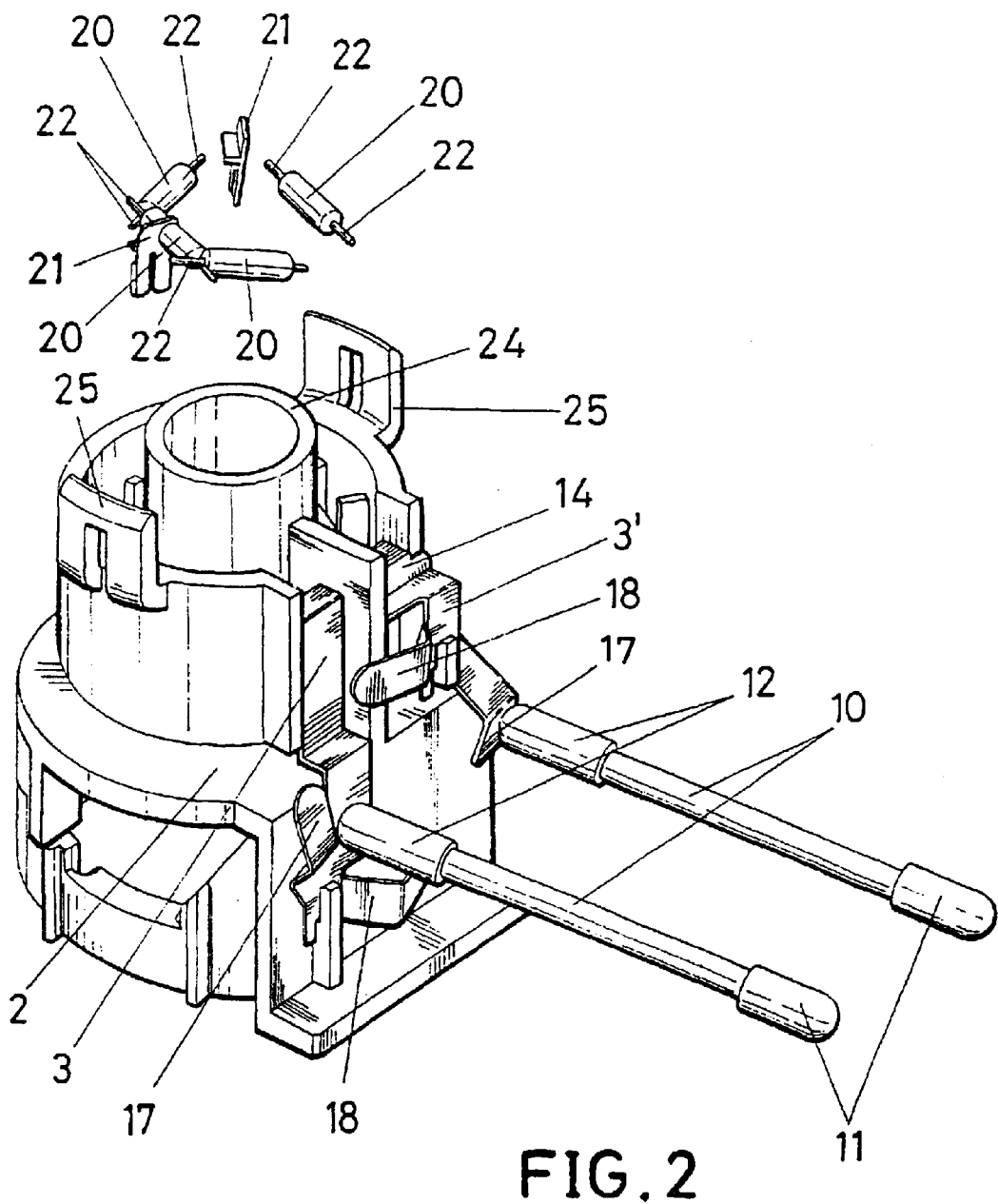
FIG. 2.—Shows a general perspective view of the inner part of the device for mounting the contacts, which are duly coupled to said part and in which are shown in an exploded view the electrical heating resistors and the two pins of the plug, although the plug body is not shown, with the inner ends of said pins meeting the contacts mounted on the aforementioned inner part.
Figure 4A:
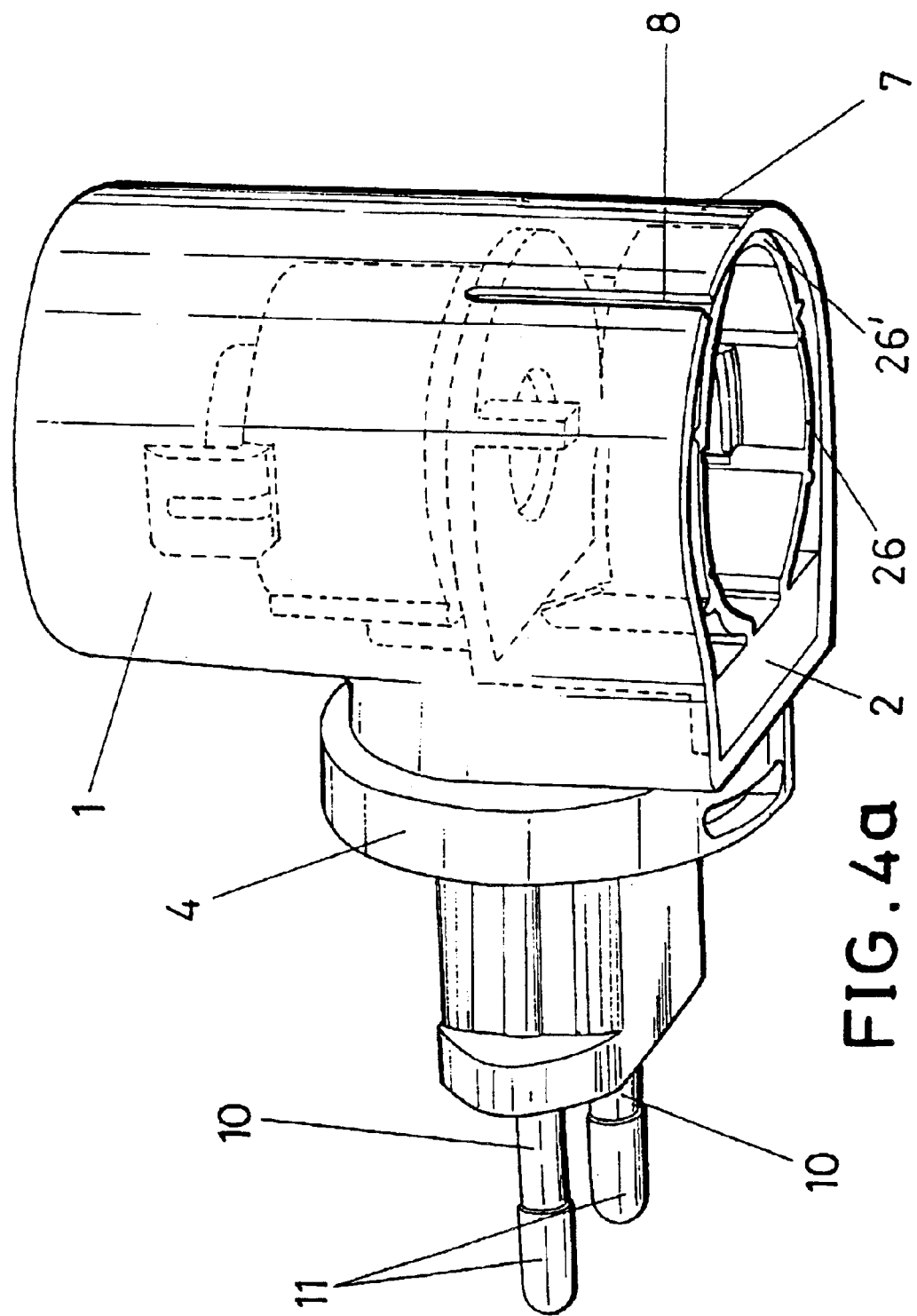
FIGS. 4a and 4b.—Show, finally, a perspective view of the entire device assembled and in an exploded view, clearly showing the case, the plug and in a discontinuous line the inner part which bears the contacts, provided with the passage neck in which is placed the wick which must be heated for evaporation of the active substance contained in the corresponding vessel which can be connected to and retained on the bottom part of the device itself.
Figure 4B:
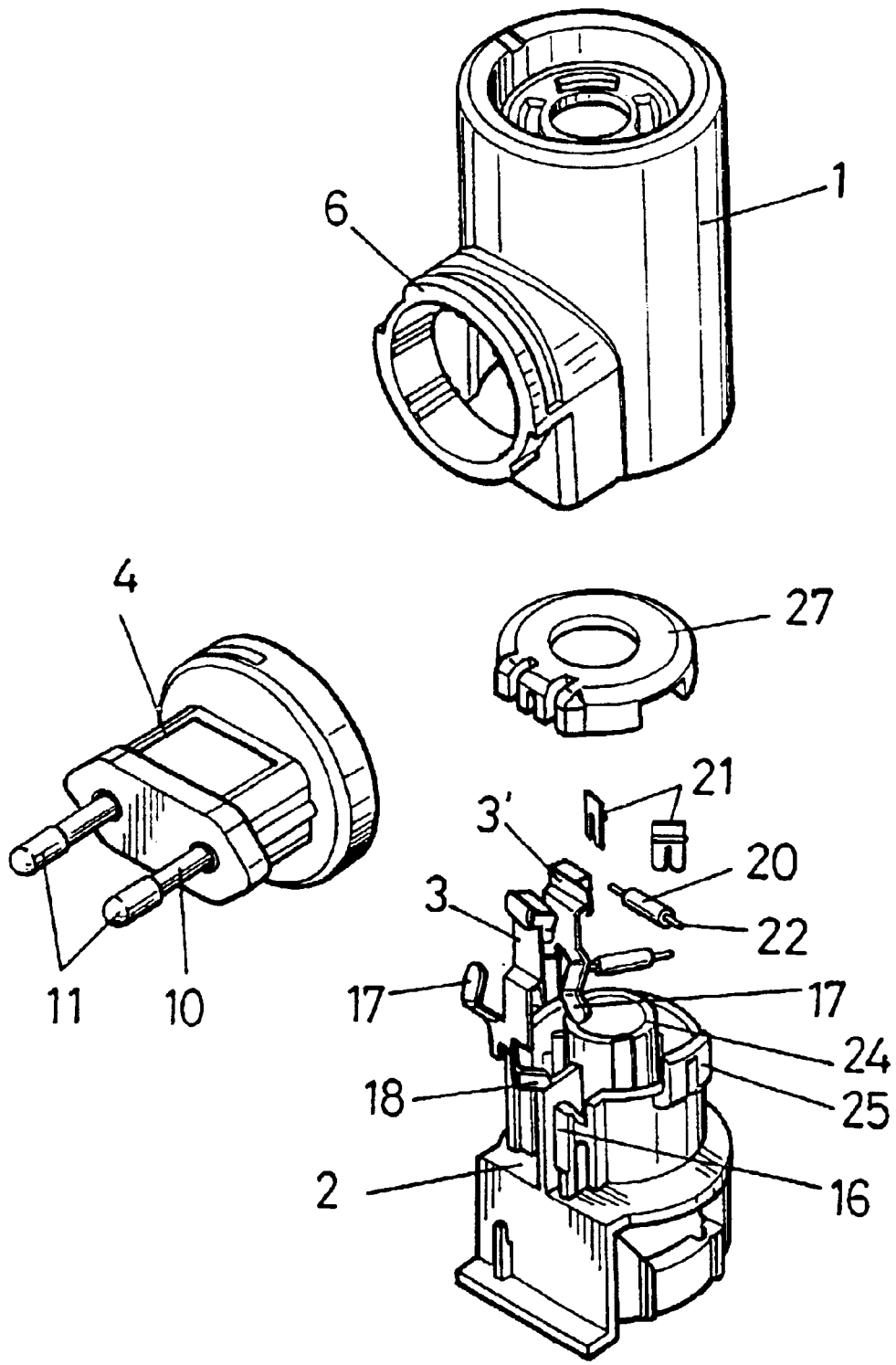

Contacts (3) and (3') are provided on one of their ends with a sort of bridge (14) in which are established oblique tabs (15), such that by means of this bridge contacts (3) and (3') are mounted on walls (16) provided for such purpose in inner part (2), as said walls (16) are placed inside bridges (14) provided at the top end of contacts (3) and (3'), with the latter being perfectly retained and placed inside part (2) as shown clearly in FIG. 2.

Additionally, contacts (3) and (3') have arced projections (17) and (18) which have a configuration and arrangement such that they form pairs of contacts which, depending on the position adopted by jack plug (4), will contact the inner ends (12) of pins (10) of said plug (4), so that when these inner elements (12) of the of the plug rest on projections (18) of contacts (3) and (3'), the plug will provide electrical continuity to the device, in adopting a horizontal position, while if the plug (4) is rotated 90° from such position the inner ends (12) of pins (11) of plug (4) will contact projections (18), also establishing electrical continuity, and thus the device may be operated in these two positions of the plug (4), that is, both horizontal and vertical, and thereby adapt to any type of socket currently commercialized.

However, if plug (4) is placed by rotation about casing (1) in a position in between the two above described positions, that is at an angle of 45° to them, the ends (12) of said plug (4) will be opposite segments (19) located between projections (17) and (18), which segments (19) are in an inner or more recessed plane, and thus ends (12) will not reach contacts (3) and (3'), thereby attaining the deactivated position without requiring any type of switch.

Naturally, contacts (3) and (3') will be connected to the corresponding electrical resistors (20) which may be secured by zero, one or two clips (21), and whose excess wire (22) by which the corresponding connections are performed are pushed by this special configuration of bridges (14) and tabs (15) of contacts (3) and (3') against grooves (23) provided for such purpose in walls (16) for mounting contacts (3) and (3'), so that these ends of excess wire (22) of resistors (20) are folded and straightened in the position corresponding to grooves or slots (23).

As regards the inner part (2), in addition to the already described characteristics it is provided with a corresponding passage neck (24) for placing the wick of the vessel which contains the active substance, which must be mounted on the bottom of the device unit, with said part (2) secured to the inside of casing (1) by pins (25) placed on the inner or top end of part (2) and which lock inside casing (1), thereby securing it without the possibility of extraction without breaking the unit.

Lastly, said part (2) is provided in its bottom end with an elastic ring (26), oval in shape, between whose proximal or lateral sides is retained, by its neck, the vessel containing the substance to be evaporated, and in which vessel is naturally provided a wick which emerges upwards through a passing neck (24) of part (2), so that this wick is heated by resistances (20) located around it, causing its heating and thereby the evaporation of the liquid or substance which by capillary action rises to the top of the wick placed as mentioned above. In order to release the vessel from ring (26) it suffices to press inwards from the outside on elastic sector (7) of casing (1), which pressure involves the inwards deformation of sector (7) and thereby pushes on segment (26') of ring (26), separating the sides of the ring and thereby releasing the vessel.

What is claimed is:

1. A heater device for active substances, for holding a vessel containing a vaporizable substance, in which vessel is a wick through which by capillary action the vaporizable substance rises and reaches the end of said wick, said wick having an end extending from the vessel said wick end being placed in a corresponding neck of the heater device in which are provided heating elements for the wick, so that the heat generated causes the evaporation of the vaporizable substance, provided with means for electrical power supply, the heater device comprising:

an external casing, an inner part, a jack plug, and first and second contact elements which form a third element, said third element being secured and mounted on the inner part wherein the heating elements include corresponding electrical resistors that are directly connected to the first and second contact elements, the first and second contact elements facing each other so that they may make contact with inner ends of pins of the jack plug, while the jack plug is retained inside a lateral neck of the casing such that it cannot move axially but may rotate to occupy two positions at 90° to each other, in which contact is made with the first and second elements, and an intermediate position in which the inner ends of the pins of the jack plug are not in contact with the first and second contact elements.

2. The heater device as claimed in claim 1, characterized in that an inner part of the lateral neck is provided with ribs which define a means of retention for projections on an inner face of a body of the jack plug, such that the jack plug cannot move axially but may rotate about itself.

3. The heater device as claimed in claim 1, characterized in that the external casing is provided with a means for retaining corresponding tabs which lock the inner part inside the external casing, which casing is provided with a pair of axial slits which is defined an elastic sector which when pressed results in a deformation of an elastic ring which is placed on the bottom of the inner part for support and retention of the vessel containing the active substance, with the deformation of said elastic ring resulting in the release of said vessel.

4. The heater device as claimed in claim 3, characterized in that the inner part is provided with a corresponding neck for the wick, pins for anchoring and securing it inside the external casing and walls on which are mounted and secured the first and second contact elements, through bridges placed on one end of each of the first and second contact elements.

5. The heater device as claimed in claim 4, characterized in that in correspondence with the bridges for mounting the first and second contact elements on walls of the inner part, are provided internal oblique tabs which support the corresponding electrical resistors, the corresponding electrical resistors having excess wire ends left after their connection that are inserted and straightened in grooves made in the walls for mounting the first and second contacts.

6. The heater device as claimed in claim 1, characterized in that the first and second contact elements have pairs of bent projections, with a suitable configuration and arrangement for determining connection pairs of the inner ends of the jack plug, in accordance with a rotational position of the jack plug with respect to the external casing, establishing between projections of each of the first and second contact elements a segment which is recessed with respect to the bent projections, so that in an intermediate rotation position of the jack plug, ends of pins of the jack plug are separated from the segments of the first and second contact elements without making contact with the first and second contact elements in the intermediate position, the intermediate position corresponding to an inoperative position of the jack plug that is engaged without requiring an additional switch.

7. The heater device as claimed in claim 1, characterized in that the heater device further includes a part that houses the corresponding heating elements and support elements corresponding to said heating elements.

* * * * *